: US009265473B2

(12) United States Patent
Mittal et al.

(10) Patent No.: US 9,265,473 B2
(45) Date of Patent: Feb. 23, 2016

(54) METHOD FOR ESTIMATING FLOW RATES AND PRESSURE GRADIENTS IN ARTERIAL NETWORKS FROM PATIENT SPECIFIC COMPUTED TOMOGRAPHY ANGIOGRAM-BASED CONTRAST DISTRIBUTION DATA

(71) Applicant: The Johns Hopkins University, Baltimore, MD (US)

(72) Inventors: Rajat Mittal, Vienna, VA (US); Albert C. Lardo, Baldwin, MD (US); Jung Hee Seo, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/204,264

(22) Filed: Mar. 11, 2014

(65) Prior Publication Data

US 2014/0243662 A1    Aug. 28, 2014

Related U.S. Application Data

(63) Continuation-in-part of application No. 13/868,697, filed on Apr. 23, 2013.

(60) Provisional application No. 61/705,422, filed on Sep. 25, 2012.

(51) Int. Cl.
*A61B 5/05*  (2006.01)
*A61B 6/00*  (2006.01)
(Continued)

(52) U.S. Cl.
CPC ............... *A61B 6/504* (2013.01); *A61B 5/0044* (2013.01); *A61B 5/026* (2013.01);
(Continued)

(58) Field of Classification Search
USPC ......... 600/410, 425, 438, 454, 458, 468, 504; 703/9
See application file for complete search history.

(56) References Cited

U.S. PATENT DOCUMENTS

2006/0206032 A1   9/2006  Miele et al.
2010/0234698 A1   9/2010  Manstrom et al.
2010/0241000 A1   9/2010  Kondo et al.

FOREIGN PATENT DOCUMENTS

WO           0121057 A2    3/2001

OTHER PUBLICATIONS

Choi, J., et al., "Intracoronary transluminal attenuation gradient in coronary CT angiography for determining coronary artery stenosis", JACC: Cardiovascular Imaging, vol. 4, No. 11, Nov. 1, 2011, pp. 1149-1157.

(Continued)

*Primary Examiner* — Unsu Jung
*Assistant Examiner* — Michael N Fisher
(74) *Attorney, Agent, or Firm* — Johns Hopkins Technology Transfer

(57) ABSTRACT

An embodiment in accordance with the present invention provides a method for non-invasively determining the functional severity of arterial stenosis in a selected portion of an arterial network. The method includes gathering patient-specific data related to concentration of a contrast agent within an arterial network using a coronary computed tomography angiography scan (CCTA). The data can be gathered under rest or stress conditions. Estimation of a loss coefficient (K) can be used to eliminate the need for data gathered under stress. The data is used to calculate a transluminal attenuation gradient (TAG). The data may be corrected for imaging artifacts at any stage of the analysis. TAFE is used to determine an estimate of flow velocity. Once velocity is determined, pressure gradient, coronary flow reserve, and/or fractional flow reserve can be determined through a variety of methods. These estimates can be used to estimate functional severity of stenosis.

22 Claims, 17 Drawing Sheets

(51) Int. Cl.
  *A61B 6/03* (2006.01)
  *A61B 5/00* (2006.01)
  *A61B 5/02* (2006.01)
  *A61B 5/026* (2006.01)
  *G06T 7/00* (2006.01)

(52) U.S. Cl.
  CPC ............ *A61B 5/02007* (2013.01); *A61B 6/032* (2013.01); *A61B 6/481* (2013.01); *A61B 6/507* (2013.01); *A61B 6/5205* (2013.01); *A61B 6/5217* (2013.01); *G06T 7/0016* (2013.01); *G06T 2207/10076* (2013.01); *G06T 2207/10081* (2013.01); *G06T 2207/30076* (2013.01); *G06T 2207/30104* (2013.01)

(56) References Cited

OTHER PUBLICATIONS

International Search Report and Written Opinion, mailed Aug. 23, 2013; PCT/US2013/037804 filed Apr. 24, 2013.

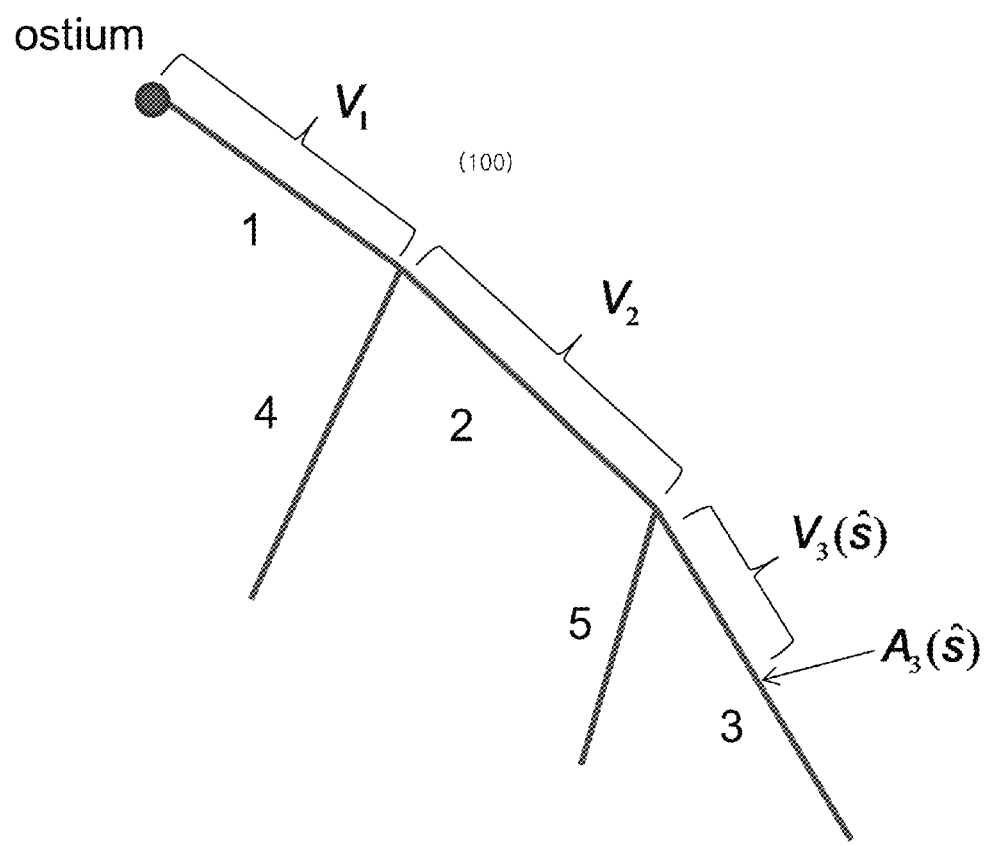

| | $V_{(s)}$ (mL) | $V_{vessel}$ (mL) | $A$ (cm²) | $T_d$ (sec) | TAG* (/cm) | TAG** (sec²/mL) | $\tau$ (sec) | $Q_{TAPE}$ (mL/sec) | $Q_{CFD}$ (mL/sec) |
|---|---|---|---|---|---|---|---|---|---|
| S1 | 0.5643 | 1.13E+00 | 2.40E-01 | 10 | -1.69E-04 | 0.0142615 | 0 | 6.29 | 6.59 |
| S2 | 1.31476 | 3.85E-01 | 1.74E-01 | 10 | -3.40E-04 | 0.0394841 | 0.18038 | 5.41 | 5.78 |
| S3 | 1.86992 | 6.91E-01 | 1.48E-01 | 10 | -5.60E-04 | 0.0768063 | 0.25145 | 4.33 | 4.49 |
| S4 | 2.63869 | 7.75E-01 | 1.18E-01 | 10 | -1.95E-03 | 0.3360072 | 0.41119 | 1.90 | 2.12 |

METHOD FOR ESTIMATING FLOW RATES AND PRESSURE GRADIENTS IN ARTERIAL NETWORKS FROM PATIENT SPECIFIC COMPUTED TOMOGRAPHY ANGIOGRAM-BASED CONTRAST DISTRIBUTION DATA

CROSS REFERENCE TO RELATED APPLICATIONS

This application is a continuation-in-part of U.S. patent application Ser. No. 13/868,697 filed on Apr. 23, 2013, which claims the benefit of U.S. Provisional Patent Application No. 61/705,422 filed on Sep. 25, 2012, and International Application No. PCT/US2013/037804, all of which are incorporated by reference, herein, in their entirety.

FIELD OF THE INVENTION

The present invention relates generally to cardiology. More particularly, the present invention relates to a computed tomography cardiac imaging based method for determining flow rates, pressure gradients and fractional flow reserve in an arterial network.

BACKGROUND OF THE INVENTION

The coronary arteries supply the myocardium, or muscle of the heart with oxygen and nutrients. Over time the coronary arteries can become blocked with cholesterol and other material known as plaque. Coronary artery disease results from this buildup of plaque within the walls of the coronary arteries. Excessive plaque build-up can lead to diminished blood flow through the coronary arteries and low blood flow to the myocardium leading to chest pain, ischemia, and heart attack. Coronary artery disease (CAD) can also weaken the heart muscle and contribute to heart failure, a condition where the heart's efficiency as a pump is compromised. This state can lead to electrical disorders of the heart that increase the possibility for sudden cardiac death. Coronary artery disease is the leading cause of death for both men and women in the United States. CAD affects 17.6 million Americans and results in nearly half a million deaths per year. Despite access to sophisticated diagnostic imaging tests at a cost of $6.3 billion per year, over 1,000,000 US patients are referred to unnecessary invasive catheterization procedures exposing patients to inherent risks and a staggering $8 B financial burden to the US healthcare system.

There are several different diagnostics that are currently used to assess coronary artery disease and its severity. Non-invasive tests can include electrocardiograms, biomarker evaluations from blood tests, treadmill tests, echocardiography, single positron emission computed tomography (SPECT), and positron emission tomography (PET). Unfortunately, these non-invasive tests do not provide data related to the size of a coronary lesion or its specific effect on coronary blood flow, pressure gradients and fractional flow reserve.

Quantitative coronary angiography (QCA) is a well-established invasive method for visualizing and quantifying the size of an arterial lesion such as those associated with coronary artery disease. In this method, a radiopaque contrast agent is injected into the blood and an x-ray scan movie is acquired when the contrast agent has traveled into the coronary arteries. Clinicians can use this information to visually examine and to quantify the degree of obstruction. An area obstruction of greater than 70% has traditionally been considered flow-limiting and a candidate for percutaneous coronary intervention (PCI) (also known as coronary angioplasty).

While the above procedure can be used to visualize and quantify the size of the lesion or the degree of obstruction, it does not necessarily correlate to the functional significance of the lesion, i.e. the degree to which the lesion affect the rate of flow of blood through the artery. Therefore, additional assessments have been developed to determine functional significance of coronary artery lesions. In this regard catheter measured coronary flow velocity (CFV), pressure gradient (PG) i.e. the pressure difference across various arterial segments, coronary flow reserve (CFR), and fractional flow reserve (FFR) are the gold standards for assessment of the functional significance of coronary artery stenosis. These metrics are currently determined using diagnostic cardiac catheterization, an invasive procedure in which a catheter is inserted into a peripheral artery (for instance in a patient's leg) and threaded through the vasculature to the relevant areas of the coronary arteries. FFR is determined by calculating the ratio of the mean blood pressure downstream from a lesion divided by the mean blood pressure upstream from the same lesion. These pressures are measured by inserting a pressure wire into the patient during the diagnostic cardiac catheterization procedure. While this procedure provides an accurate measure of FFR for determining the functional severity of the coronary stenosis, it incurs the risk and cost of an invasive procedure.

Advances in multi-detector computed tomography (CT) technology now allows noninvasive access to several important factors in regards to coronary event risk: the overall coronary arterial plaque burden, the severity of coronary arterial stenoses, the location and consistency of plaque, and plaque configuration. While anatomic information on CAD by CT is important and has been shown to correlate with patient outcomes, there are other important determinants of patient outcome with CHD including the degree of epicardial blood flow reduction and the extent and severity of provocable myocardial ischemia. CT allows the assessment of coronary anatomy, coronary blood flow, and myocardial perfusion and thus, is uniquely positioned to acquire comprehensive information to guide the evaluation and management of patients with suspected CHD.

While coronary CTA has been shown to be an accurate test to diagnose the presence of coronary atherosclerosis and percent stenosis it has been shown to poorly predict myocardial ischemia compared to invasive and non-invasive standards. Compared to positron emission tomography, a 50% stenosis by CTA has a positive predictive value for myocardial ischemia of 26% a finding that has been reproduced in a number of studies. Compared to FFR, the invasive gold standard for determining the physiologic significance of a stenosis, percent stenosis by CTA shows only a moderate overall correlation (r=0.55) and no significant correlation with lesions ≤10 mm in length (r=0.16).

FFR can also be estimated based on a highly complex computational fluid dynamics (CFD) modeling in CT derived, patient-specific coronary artery models. This approach by HeartFlow Inc. and called $FFR_{CT}$™ requires a high level of sophistication, is computationally intensive, and generally requires that patient-specific data be transmitted out of the hospital environment to a third party vendor. It is also expensive and can take several days to obtain results. Additionally, recent data testing this approach to predict actual FFR in a multicenter trial have been disappointing. For instance, the study did not meet its pre-specified primary endpoint, which was diagnostic accuracy of >70% of the lower bound of the one-sided 95% CI. One factor contributing to the computational complexity as well as the reduced accuracy of this approach is the lack of precise boundary and input conditions for velocity/flow rate for the artery of interest. An attempts to overcome this is made in $FFR_{CT}$™ by combining a variety of information including patient-specific ventricular mass, resting coronary flow from population derived relationships and population derived measures of coronary resistances. The above information is combined with physiologic data such as blood pressure, heart rate and computational fluid dynamic (CFD) modeling of the ascending aorta and all the major coronary vessels. This CFD model is also connected with the rest of the circulatory system via lumped-element (or "windkessel") models which contain a number of population derived parameters. However, this approach necessitates the use of ad-hoc parameters and generic (non-patient-specific) factors which can reduce the accuracy of the computed FFR. The quality of the CFD solution is highly sensitive to the computational grid that is employed and the need to generate a grid over the large section of the circulatory system (ascending aorta and coronary arteries) also introduces an additional source of inaccuracy and uncertainty in the results from the CFD calculation.

It would therefore be advantageous to provide an alternative non-invasive CT based method for assessing hemodynamic parameters such as determining the CFV, PG, CFR, and/or FFR for a given patient's coronary arteries. If such a method is computationally simple and relatively inexpensive, it could be implemented in the scanner or locally on a computer at the scanning facility, and the results made available within a relatively short time (order of minutes) after the completion of the scan. This would also allow the radiologist/clinician to interact in near-real time with the analysis tool. Such an approach would fundamentally change the practice of clinical cardiology and allow clinicians to accurately and rapidly identify specific vessels that are resulting in a reduction in the blood flow to the myocardium.

SUMMARY OF THE INVENTION

The foregoing needs are met, to a great extent, by the present invention, wherein in one aspect a method for determining functional significance of an arterial stenosis or lesion in a patient including determining an area of interest an arterial network of the patient. The method includes obtaining a CT scan of the patient during an angiogram procedure, resulting in data on the area of interest and using the data obtained from the CT scan to calculate an arterial input function (AIF) for the area of interest. Additionally, the method includes using the data obtained from the CT scan to determine contrast distribution and transluminal attenuation gradient (TAG) for the area of interest and calculating transluminal attenuation flow encoding (TAFE) using contrast distribution, TAG, and AIF. The method also includes modeling flow velocity using TAFE.

In accordance with an aspect of the present invention, the method includes augmenting the calculation of TAFE with data related to characteristics of the scanner used to obtain the CT scan and programming a non-transitory computer readable medium to execute the method. The method also includes bringing the patient to a rest condition before obtaining the CT scan of the patient during the angiogram and calculating the coronary flow velocity for the area of interest for the patient at the rest condition. The method also includes bringing the patient to a stressed condition before obtaining the CT scan of the patient during the angiogram and calculating the coronary flow velocity for the area of interest for the patient at the stress condition. In addition, the method includes obtaining a CT scan of the patient during an angiogram with the patient at rest and obtaining a CT scan of the patient during an angiogram with the patient under stress and calculating flow rate for the patient at rest and under stress. The method also includes calculating coronary flow reserve for the area of interest as a ratio of $Q_{stress}$ to $Q_{rest}$.

In accordance with another aspect of the present invention, a method for determining functional significance of an arterial stenosis or lesion in a patient includes determining an area of interest an arterial network of the patient and obtaining a CT scan of the patient during an angiogram procedure, resulting in data on the area of interest. The method includes using the data obtained from the CT scan to calculate an arterial input function (AIF) for the area of interest and using the data obtained from the CT scan to determine contrast distribution and transluminal attenuation gradient (TAG) for the area of interest. The method also includes calculating transluminal attenuation flow encoding (TAFE) using contrast distribution, TAG, and AIF. Additionally, the method includes modeling flow velocity using TAFE and using the coronary flow velocity to determine inflow and outflow rate and boundary conditions for the area of interest. The method includes determining 3D arterial lumen geometry, performing CFD modeling for the area of interest using the boundary conditions, inflow and outflow rates, and the 3D arterial lumen geometry, and calculating a pressure gradient for the area of interest using the CFD model. The method also includes using the pressure gradient to determine a loss coefficient for the area of interest.

In accordance with another aspect of the present invention, the method includes augmenting the calculation of TAFE with data related to characteristics of the scanner used to obtain the CT scan. The method also includes programming a non-transitory computer readable medium to execute the method.

In accordance with yet another aspect of the present invention, a method for determining functional significance of an arterial stenosis or lesion in a patient including determining an area of interest an arterial network of the patient. The method includes obtaining a CT scan of the patient during an angiogram procedure, resulting in data on the area of interest and using the data obtained from the CT scan to calculate an arterial input function (AIF) for the area of interest. The method also includes using the data obtained from the CT scan to determine contrast distribution and transluminal attenuation gradient (TAG) for the area of interest, calculating transluminal attenuation flow encoding (TAFE) using contrast distribution, TAG, and AIF, and modeling flow velocity using TAFE. Additionally, the method includes using the coronary flow velocity to determine inflow and outflow rate and boundary conditions for the area of interest, determining 3D arterial lumen geometry, performing CFD modeling for the area of interest using the boundary conditions, inflow and outflow rates, and the 3D arterial lumen geometry, calculating a pressure gradient for the area of interest using the CFD model, and using the pressure gradient to determine a loss coefficient for the area of interest. The method also includes measuring brachial pressure, calculating an absolute arterial pressure, and calculating fractional flow reserve at rest for the patient.

In accordance with another aspect of the present invention, the method includes augmenting the calculation of TAFE with data related to characteristics of the scanner used to obtain the CT scan. The method also includes programming a non-transitory computer readable medium to execute the method.

In accordance with still another aspect of the present invention, a system for determining functional significance of an arterial stenosis or lesion in a patient includes a CT scanner configurable to obtain patient specific data related to an area of interest of an arterial network of the patient. The method also includes a non-transitory computer readable medium programmed for determining an area of interest an arterial network of the patient, obtaining the patient specific data on the area of interest, and using the patient specific data obtained from the CT scan to calculate an arterial input function (AIF) for the area of interest. The non-transitory computer readable medium is also programmed for using the patient specific data obtained from the CT scan to determine contrast distribution and transluminal attenuation gradient (TAG) for the area of interest, calculating transluminal attenuation flow encoding (TAFE) using contrast distribution, TAG, and AIF, and modeling flow velocity using TAFE.

In accordance with yet another aspect of the present invention, the method includes obtaining patient specific data during an angiogram with the patient at rest and obtaining patient specific data during an angiogram with the patient under stress. The method also includes calculating flow rate for the patient at rest and under stress. Additionally, the method includes calculating coronary flow reserve for the area of interest as a ratio of $Q_{stress}$ to $Q_{rest}$. The method also includes using the coronary flow velocity to determine inflow and outflow rate and boundary conditions for the area of interest, determining 3D arterial lumen geometry, performing CFD modeling for the area of interest using the boundary conditions, inflow and outflow rates, and the 3D arterial lumen geometry, calculating a pressure gradient for the area of interest using the CFD model, and using the pressure gradient to determine a loss coefficient for the area of interest. In addition, the method includes measuring brachial pressure, calculating an absolute arterial pressure, and calculating fractional flow reserve at rest for the patient.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIG. 4 illustrates an exemplary schematic diagram of a selected portion of an arterial network, segmented, according to an embodiment of the present invention.

DETAILED DESCRIPTION

Figure 1A:
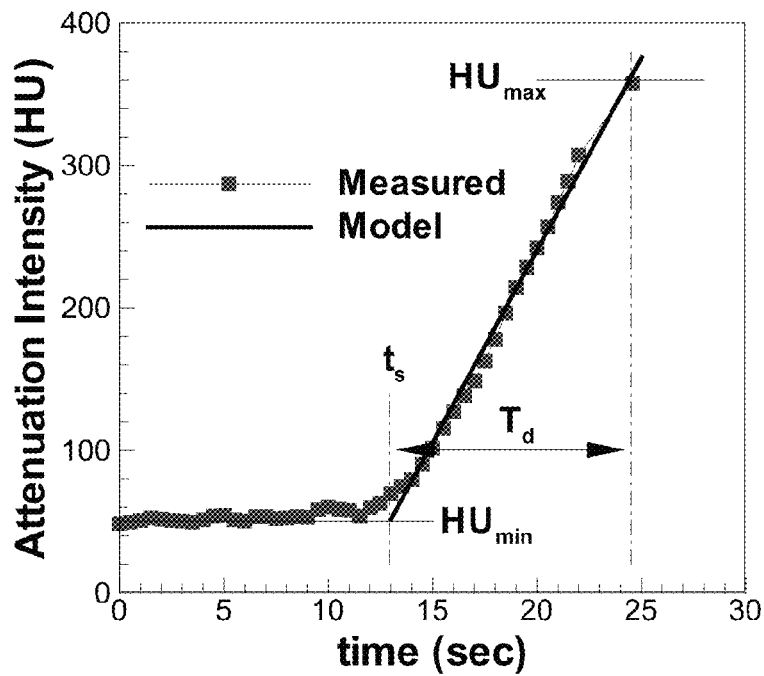
FIGS. 1A and 1B illustrate two of the many possible arterial input functions that could be considered for the derivation of transluminal attenuation flow encoding (TAFE) formulations.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention provides a method for non-invasively determining the functional severity of arterial stenosis in a selected portion of an arterial network. The method includes gathering patient-specific data related to concentration of a contrast agent within an arterial network of a patient using a coronary computed tomography angiography scan (CCTA). The patient specific data can be gathered from rest or under stress. Alternately, the use of the estimation of a loss coefficient (K) can be used to eliminate the need for data gathered under stress. The patient-specific data is used to calculate a patient-specific transluminal attenuation gradient (TAG) for a selected portion of the arterial network of the patient. The data may be corrected for imaging artifacts at any stage of the analysis. The patient specific TAG is used to determine an estimate of the arterial flow velocity, pressure gradient, arterial flow reserve, and/or fractional flow reserve for the patient. Arterial flow velocity, pressure gradient, arterial flow reserve, and fractional flow reserve can then be used to estimate the functional severity of stenosis.

Figure 1B:
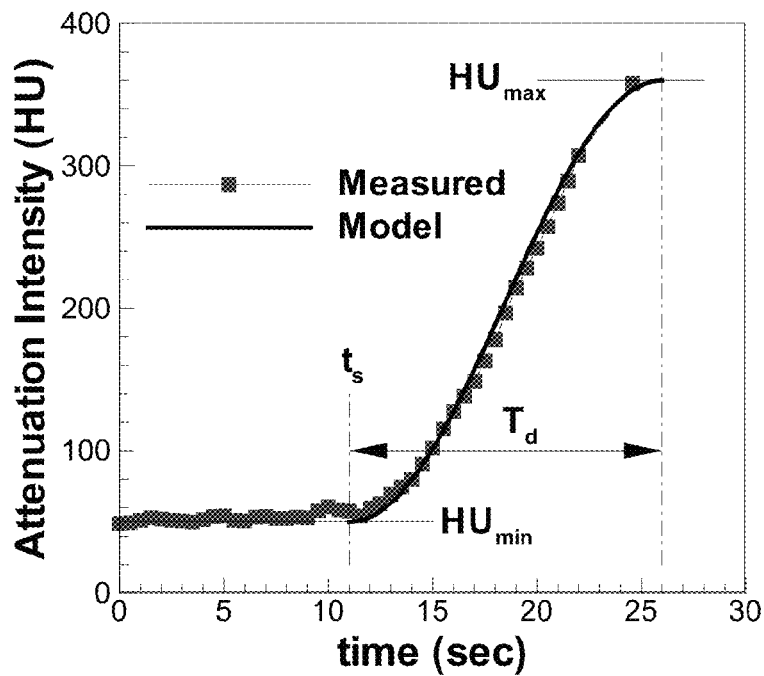

More particularly, Equation (1) represents a one-dimensional advection equation for the cross-sectional averaged contrast concentration C which is generally proportional to the arterial attenuation measured in CTCA by HU (Hounsfield Unit):

$$\frac{\partial C}{\partial t} + \frac{Q}{A}\frac{\partial C}{\partial s} \approx 0 \Rightarrow \frac{\partial C}{\partial \xi} + Q\frac{\partial C}{\partial \eta} \approx 0, \quad (1)$$

$$\xi = \int Q(t)dt = \overline{Q} \cdot t,$$

$$\eta = \int A(s)ds = \overline{A} \cdot s$$

where $C_{(t,s)}$ is a function of time (t) and axial location (s) in the artery. Assuming $\overline{Q}$ is constant, the solution of Eq. (1) can be approximated as:

$$C(t,s) \approx C_{ostium}(t - V(s)/\overline{Q}) \quad (2)$$

where $C_{ostium}$ is the time variation of concentration at s=0, i.e. coronary ostium, and we call $C_{ostium}(t)$ as an arterial input function (AIF), and V(s) is the vessel volume given by $V(s) = \int_0^s A(s)ds$. Based on Eq. (1) concentration gradient between two axial locations $s_1$ and $s_2$ in an artery, which is in fact the TAG, results in:

$$TAG = \frac{\overline{C}_{s_2} - \overline{C}_{s_1}}{s_2 - s_1} \approx -\overline{A} \cdot \frac{\partial \overline{C}}{\partial \xi} \approx -\frac{\overline{A}}{\overline{Q}} \cdot \frac{\partial}{\partial t} C_{ostium}(t - V(\hat{s})/\overline{Q}) \quad (3)$$

where $\overline{A} = V_{vessel}/L_{vessel}$ is the average cross-sectional area and $\hat{s}$ is the axial distance in the artery to the point between the two axial locations. Thus TAG is inversely proportional to the average flow rate, $\overline{Q}$, but also related to the arterial input function (AIF), $C_{ostium}(t)$. FIGS. 1A and 1B show two particular types of AIF models that we have considered. AIF profiles are available from CT scans and other representative profiles may also be employed.

The simplest approximation of the AIF is a linear ramp function (FIG. 1A);

$$C_{ostium}(t) = C_{min} + (C_{max} - C_{min})\left(\frac{t - t_s}{T_d}\right) \quad (4)$$

where $C_{max}$ and $C_{min}$ are the maximum and minimum concentrations at the ostium, $t_s$ is the arrival time of the bolus, and $T_d$ is the time-delay between the arrival of the bolus and the maximum enhancement. Substituting Equation (4) into Equation (3), the TAG at $t=t_s+T_d$ is estimated as:

$$TAG^*(cm^{-1}) = \frac{TAG}{C_{max} - C_{min}} \sim -\frac{\overline{A}}{\overline{Q} \cdot T_d} \quad (5)$$

where TAG* is TAG normalized by the density rise at the ostium with units of $cm^{-1}$. Solving for $\overline{Q}$ we arrive at a simple expression for arterial flow (ml/min) as a function of TAG*, the average cross sectional area ($\overline{A}$):

$$\boxed{\overline{Q} = \frac{\overline{A}}{(-TAG^*) \cdot T_d}} \quad (6)$$

In some cases, the AIF can be described by a non-linear function, such as for instance, a cosine function (FIG. 1B) as:

$$C_{ostium}(t) = C_{min} + \tfrac{1}{2}(C_{max} - C_{min})[1 - \cos(\pi(t-t_s)/T_d)] \quad (7)$$

where $C_{max}$ and $C_{min}$ are the maximum and minimum concentrations at the ostium, $t_s$ is the arrival time of the bolus, and $T_d$ is the time-delay between the arrival of the bolus and the maximum enhancement. Substituting Equation (7) into Equation (3), the TAG at $t=t_s+T_d$ is estimated as:

$$TAG^*(cm^{-1}) = \frac{TAG}{C_{max} - C_{min}} \sim -\frac{1}{2}\frac{\overline{A}}{\overline{Q}}\frac{\pi}{T_d}\sin\left(\frac{\pi V(\hat{s})}{T_d \overline{Q}}\right) \quad (8)$$

$$\approx -\frac{1}{2}\left(\frac{1}{\overline{Q}^2}\right)\left(\frac{1}{T_d^2}\right)\pi^2 \overline{A} V(\hat{s})$$

where TAG* is TAG normalized by the density rise at the ostium with units of $cm^{-1}$. Solving for $\overline{Q}$ we arrive at a simple expression for arterial flow (ml/min) as a function of TAG*, the average cross sectional area ($\overline{A}$), vessel volume ($V(\hat{s})$) and the bolus duration $T_d$;

$$\boxed{\overline{Q} = \frac{\pi}{T_d}\sqrt{\frac{\overline{A} V(\hat{s})}{-2(TAG^*)}}} \quad (9)$$

Figure 2:
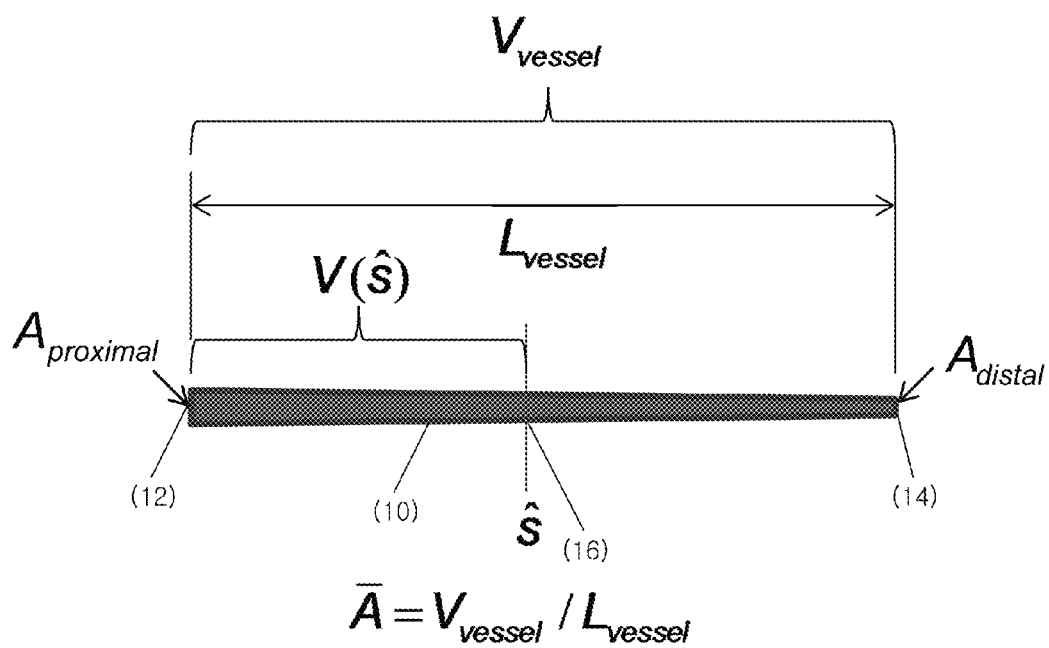
FIG. 2 illustrates a schematic diagram of a blood vessel, according to an embodiment of the present invention.

All of the parameters in the above equation are readily available using current conventional CTA exams. The calculation of $\overline{Q}$, as in Eqs. (6) and (9) (as well as other related equations) can also be referred to as transluminal attenuation flow encoding (TAFE). FIG. 2 illustrates a schematic diagram of a blood vessel, labeled with the above parameters. As illustrated in FIG. 2, the vessel segment (10) has a proximal end (12) and a distal end (14) and a vessel length $\hat{s}$ extending at least partially there between. The average cross sectional area $\overline{A}$ can be calculated with the total vessel volume and the vessel length. Vessel volume V can also be determined for the entire vessel, and particularly over vessel length $\hat{s}$ (16).

Figure 3A:
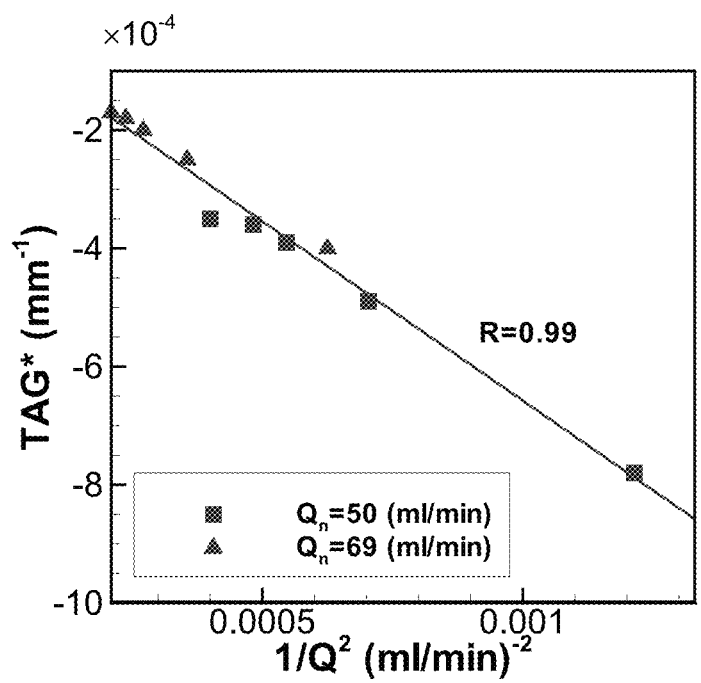
FIGS. 3A-3B illustrate the relationship between flow and transluminal attenuation gradient (TAG) and TAG and bolus duration, according to an embodiment of the present invention.
Figure 3B:
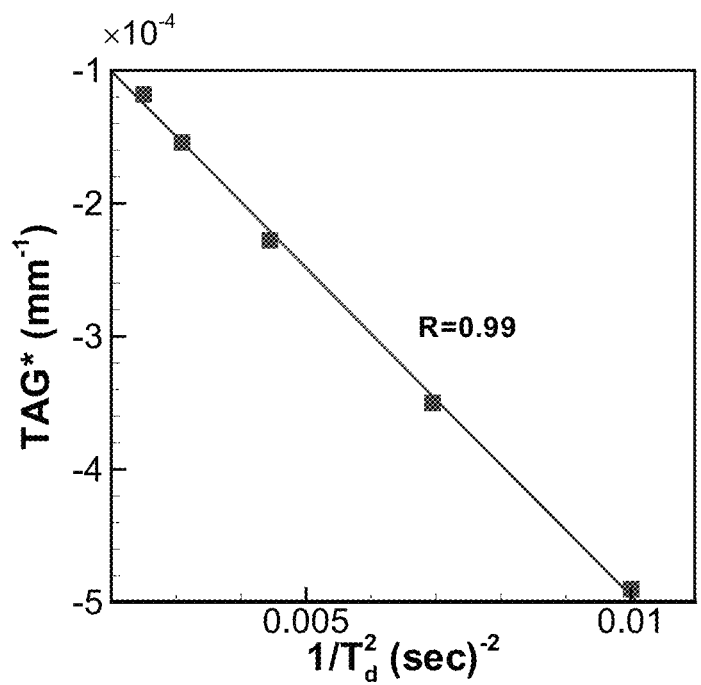

By way of example, CFD simulations of contrast dispersion dynamics were performed with the cosine AIF (Eq. 7) in simple models of coronary artery stenosis under physiologic flow conditions to confirm the proposed relationship between TAG and AIF and the fundamental relationship between flow and TAG, as illustrated in FIGS. 3A-3B. These data demonstrate the effect of AIF duration ($T_d$) on TAG and confirm the linear relationship between TAG and $1/Q^2$ detailed in Equation (8).

In order to formulate TAFE for an arterial network, first the connectivity of segments of the selected portion of the arterial network, should be identified. FIG. 4 illustrates an exemplary schematic diagram of a selected portion of an arterial network, segmented, according to an embodiment of the present invention. As illustrated in FIG. 4, the arterial network (100) includes segments labeled with (1)-(5). For the linear ramp function AIF (Eq. 4), Eqs. (5) and (6) can be applied to any segments without modification. For the cosine function AIF (Eq. 7), the retarded time for each segment should be considered. Equation (10) shows the representation of TAG for an arbitrary segment (n) in the arterial network for the cosine AIF.

$$TAG_n \approx -\frac{A_n(\hat{s})}{Q_n} \cdot \frac{\partial}{\partial t} C_{ostium}\left(t - \frac{V_n(\hat{s})}{Q_n} - \sum_{upstream} \frac{V_j}{Q_j}\right) \quad (10)$$

Here the summation for the upstream segments should include all the segments up to the coronary ostium. Equation (11) shows the representation of TAG for the segment labeled (3) in the exemplary arterial network. Note that the upstream segments of (3) up to the coronary ostium are (1) and (2).

$$TAG_3 \approx -\frac{A_3(\hat{s})}{Q_3} \cdot \frac{\partial}{\partial t} C_{ostium}\left(t - \frac{V_3(\hat{s})}{Q_3} - \frac{V_2}{Q_2} - \frac{V_1}{Q_1}\right) \quad (11)$$

Based on the above representation, TAFE based Q can also be determined for a selected portion of an arterial network, as described in the equations below. From Eq. (10), TAG for the segments (n) is given by Equation (12), $$TAG_n^* \approx -\frac{A_n(\hat{s})}{2} \frac{\pi^2}{T_d^2} \frac{1}{Q_n}\left(\frac{V_n(\hat{s})}{Q_n} + \sum_{upstream} \frac{V_j}{Q_j}\right) \quad (12)$$

Here we define scaled TAG which has units of (sec$^2$/mL), $$TAG_n'' = \frac{-2 \cdot TAG_n^*}{A_n(\hat{s})} \frac{T_d^2}{\pi^2} \quad (13)$$

and the branch retarded time, $\tau$ (sec)

$$\tau = \sum_{upstream} \frac{V_j}{Q_j}. \quad (14)$$

Finally, the flow rate through the specific arterial segment is given by $$Q_n = \frac{\tau + \sqrt{\tau^2 + 4 \cdot TAG_n'' \cdot V_n(\hat{s})}}{2 \cdot TAG_n''}. \quad (15)$$

Equation (12) represents the formula for flow estimation in the segment, n of the selected portion of the arterial network.

If the detailed information on the cross-sectional area variation, A(s), is not available, vessel volumes can be estimated with only proximal and distal cross-sectional areas by assuming linear tapering. For a tapered vessel schematically illustrated in FIG. 2, the entire vessel volume can be estimated by $$V_{vessel} = \frac{L_{vessel}}{3} \times \left(A_{proximal} + A_{distal} + \sqrt{A_{proximal}A_{distal}}\right), \quad (16)$$

where $A_{proximal}$ and $A_{distal}$ are cross sectional areas at the proximal end (12) and distal end (12), respectively. The vessel volume only up to halfway in the axial direction $V(\hat{s})$ is given by $$V(\hat{s}) = \frac{L_{vessel}}{2} \times \left(\frac{1}{2}A_{proximal} + \frac{1}{12}A_{distal} + \frac{1}{3}\sqrt{A_{proximal}A_{distal}}\right), \quad (17)$$

Here examples of coronary flow rate estimation are given for an exemplary arterial network illustrated in FIG. 4. For the linear ramp function AIF, the flow rate through each segment can be estimated by using the same formulation with Eq. (6);

$$Q_n = \frac{\bar{A}_n}{(-TAG_n^*) \cdot T_d}, \quad (18)$$

For the cosine function AIF, the flow rate is estimated by applying Eq. (15). Since the first segment labeled (1) has no upstream segments, the flow rate $Q_1$ is given by TAFE as $$Q_1 = \sqrt{\frac{V_1(\hat{s})}{TAG_1''}}, \quad (19)$$

where $V_1(\hat{s})$ can be determined using Equation (14) and $TAG_1''$ is determined using Equation (13). Note that Eq. (19) is derived from Eq. (15) with $\tau=0$. Now $Q_2$ for the segment labeled (2) is given by directly from Eq. (15) as $$Q_2 = \frac{\tau_1 + \sqrt{\tau_1^2 + 4 \cdot TAG_2'' \cdot V_2(\hat{s})}}{2 \cdot TAG_2''}, \tau_1 = \frac{V_1}{Q_1} \quad (20)$$

where $\tau_1$ is determined using Equation (14) using $V_1$ and $Q_1$, as the first vessel segment labeled (1) precedes the second vessel segment labeled (2). Similarly, $Q_3$ for the third segment labeled (3) is determined by $$Q_3 = \frac{\tau_2 + \sqrt{\tau_2^2 + 4 \cdot TAG_3'' \cdot V_3(\hat{s})}}{2 \cdot TAG_3''}, \tau_2 = \frac{V_1}{Q_1} + \frac{V_2}{Q_2} \quad (21)$$

$\tau_2$ is calculated using a summation of $V_j$ and $Q_j$, as both the first segment (1) and the second segment (2) precede the third segment (3). $Q_4$ for the segment labeled (4) is determined by $$Q_4 = \frac{\tau_1 + \sqrt{\tau_1^2 + 4 \cdot TAG_4'' \cdot V_4(\hat{s})}}{2 \cdot TAG_4''}, \tau_1 = \frac{V_1}{Q_1} \quad (22)$$

Since the upstream segment to the ostium for the segment (4) is only the segment (1), the branch retarded time for the segment (4) is the same with $\tau_1$. Finally, $Q_5$ for the segment labeled (5) is given by $$Q_5 = \frac{\tau_2 + \sqrt{\tau_2^2 + 4 \cdot TAG_5'' \cdot V_5(\hat{s})}}{2 \cdot TAG_5''}, \tau_2 = \frac{V_1}{Q_1} + \frac{V_2}{Q_2} \quad (23)$$

Note that the upstream segments for the segment (5) are (1) and (2).

Figure 5A:
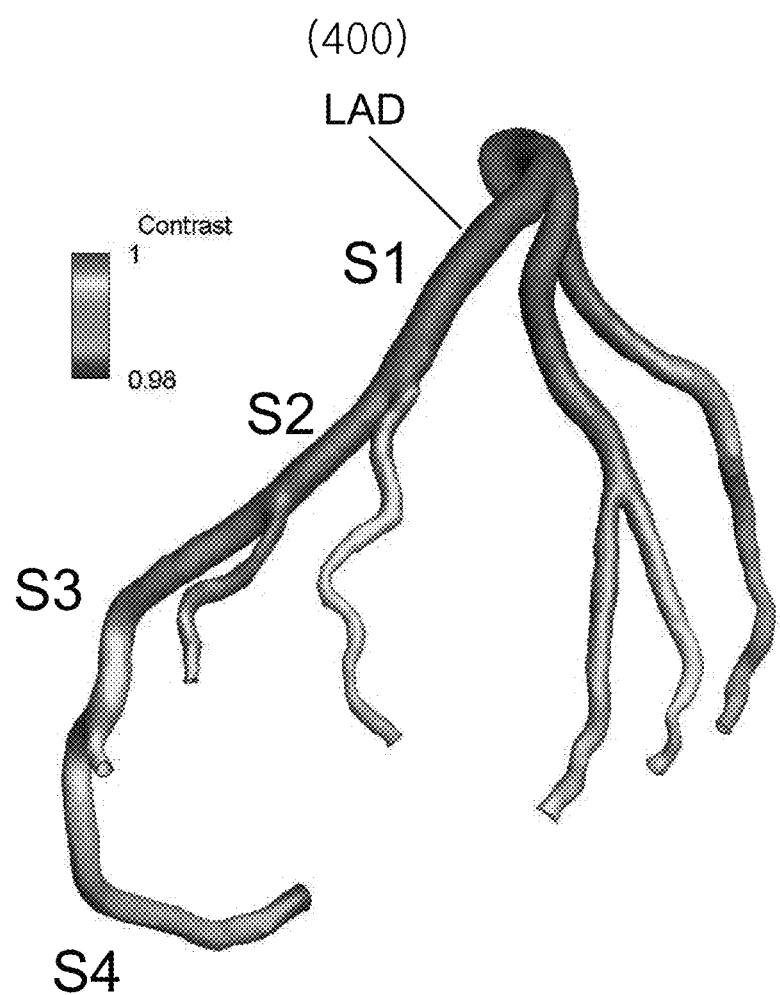
FIGS. 5A-5C illustrate a quantitative example of determining Q from TAFE formulation, according to an embodiment of the present invention.
Figures 5B, 5C:
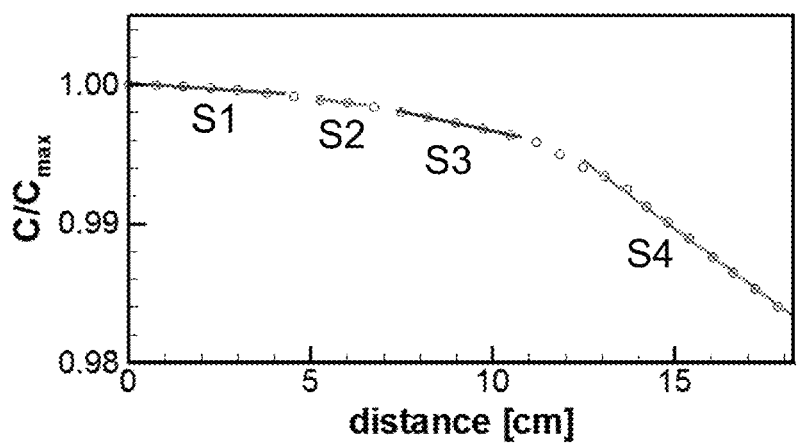

FIG. 5 illustrate a quantitative example of determining Q for the real coronary artery model simulation. FIG. 5A shows the computational fluid dynamics (CFD) simulation results for the flow and contrast dispersion in the real coronary artery model made with CT-scan data. The main LAD (left anterior descending) branch (400) includes four segments S1~S4 with 3 bifurcations. FIG. 5B shows the normalized contrast dispersion along the LAD branch (400). FIG. 5C is the table showing the estimation of flow rate through each segments (S1~S4) using the formulation (12), and the estimated flow rates, $Q_{TAFE}$ are compared with the actual flow rate obtained by full CFD simulation, $Q_{CFD}$.

Figure 6:
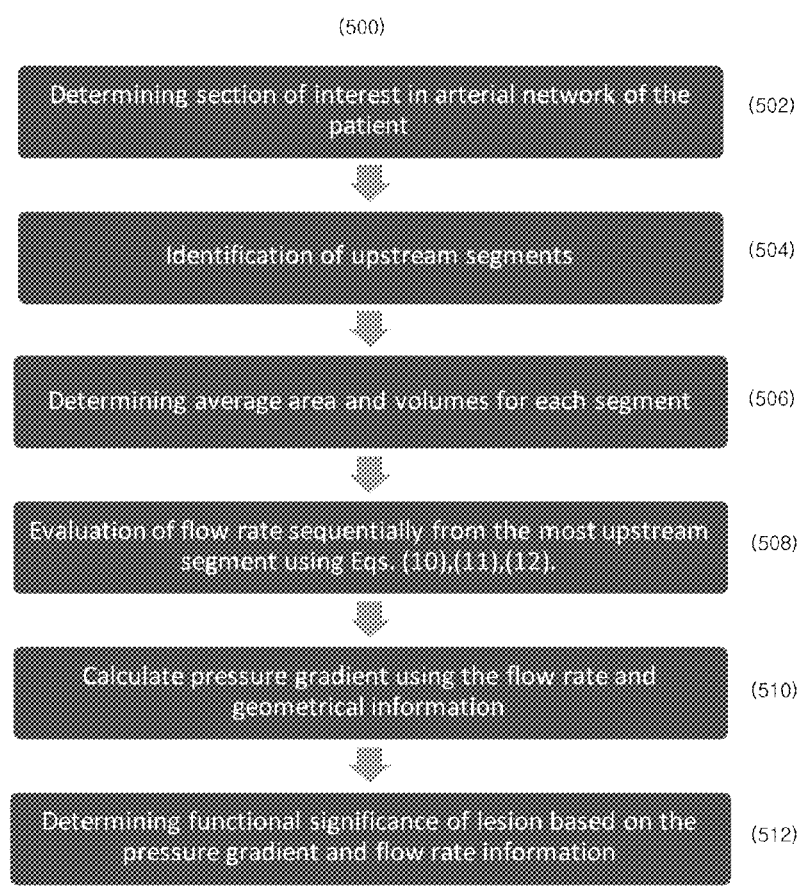
FIG. 6 illustrates a flow diagram detailing steps in accordance with a method 500 of the present invention.

FIG. 6 illustrates a flow diagram detailing steps in accordance with a method (500) of the present invention. Step (502) includes determining at least one section of interest of an arterial network of the patient. In turn, step (504) includes identification of at least one upstream segment for each arterial segment in the arterial network. The average areas and volumes for each selected segment are determined using the coronary angiography data in step (506). The flow rate in each segment should be determined sequentially from the most upstream branch with Eqs. (13), (14), (15) in step (508). The pressure gradient in each segment can be calculated by using the flow rate and the geometrical information in step (510). Pressure gradient can be used to determine the functional significance of the arterial stenosis. These steps can be carried out for a given patient in rest and stressed conditions and the flow rate and/or pressure information obtained from these two conditions provides another measure of functional significance of the stenosis. These steps can also be carried out using a computer, non-transitory computer readable medium, or alternately a computing device or non-transitory computer readable medium incorporated into the CT scanner. Indeed, any suitable method of calculation known to or conceivable by one of skill in the art could be used. It should also be noted that while specific equations are detailed herein, variations on these equations can also be derived, and this application includes any such equation known to or conceivable by one of skill in the art. A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape.

In CT angiography, the spatial resolution of the CT image is limited by the voxel size of the scanner, which for a modern multi-detector CT scanner is about 0.5 mm³. This implies for instance that the lumen of a 2 mm diameter section of an artery would be resolved by only about 12 voxels, as illustrated in FIG. 7B. The voxels at the outer edges of the lumen may be partially located outside the lumen leading to errors in the estimation of the average attenuation factor at any given cross-section. This "mixing" of densities from different structures into the same voxel is known as partial volume-averaging (PVA) and is an inherent limitation for all tomographic imaging modalities.

Figure 7A:
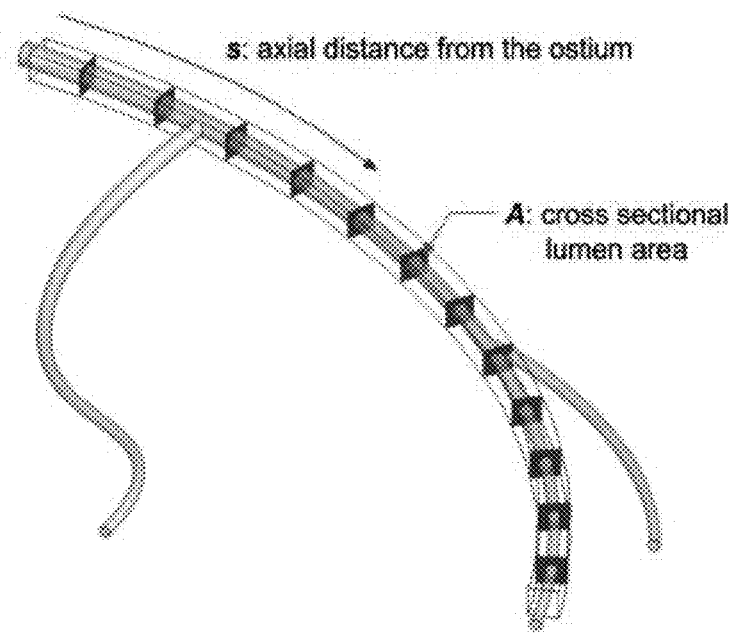
FIGS. 7A-7B illustrate a method for assessing partial volume averaging effect from CFD data, according to an embodiment of the present invention.
Figure 7B:
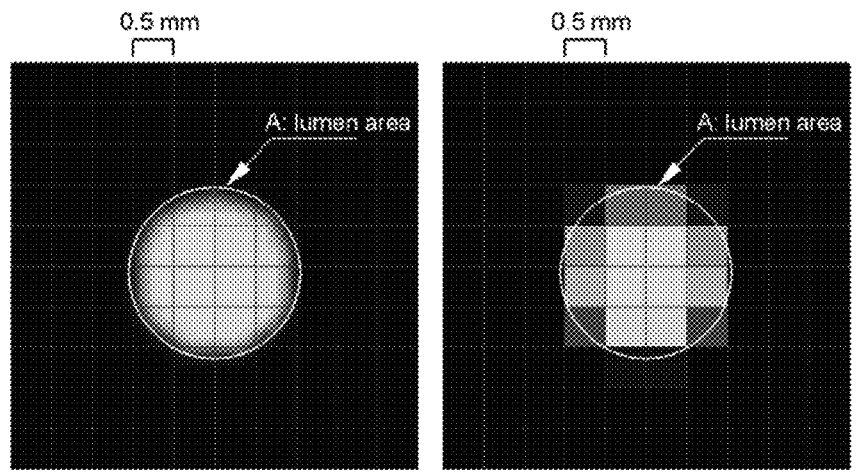

To assess these effects from CFD data, the simulation domain is embedded in a virtual voxel lattice and the mean attenuation value is reevaluated at a given axial location (s), as illustrated in FIG. 7. This procedure mimics the estimation of attenuation in CTCA and $HU_{voxel}*$ incorporates the effect of PVA inherent in these measurements. Using this approach a simple initial simulation is performed to estimate the effect of PVA and its effect on TAG for a case with area constriction of 70%, as illustrated in FIGS. 5A and 5B. More particularly, FIGS. 7A-7B illustrate a method for assessing partial volume averaging effect from CFD data. FIG. 7A illustrates multiple cross sectional slices in a CFD modeled vessel with a decreasing luminal area. The two cross sectional views illustrated in FIG. 7B represent simulated CT attenuation according to equations for the theoretical attenuation result considering a 0.5 mm³ voxel size without and with partial volume averaging, respectively using the following equations.

$$HU_{voxel}(s) = \frac{1}{N_{lumen}(s)} \sum_{i=1}^{N_{lumen}} HU_i, \quad HU_i = \frac{1}{V_i} \int C dV, \quad (24)$$

$$HU_{voxel}^* = HU_{voxel}(s) / HU_{voxel,ostium}$$

where $HU_{voxel}(s)$ is the mean attenuation value at a given axial location, s. $N_{lumen}$ is number of voxels covering the lumen at the axial location, s, and $HU_i$ is the average attenuation for the i-th voxel, $V_i$ is the volume of the voxel, $HU_{voxel}*$ is the normalized mean attenuation value and C is the iodine concentration. Results indicate that PVA effect combines with vessel taper to increase the measured TAG and the combination of PVA and vessel curvature/tortuosity generates spurious fluctuations in the attenuation profile. However CFD modeling, which may be coupled with ex-vivo phantom studies can be used to compensate TAFE formulations for PVA effects, described further, herein.

Figure 8:
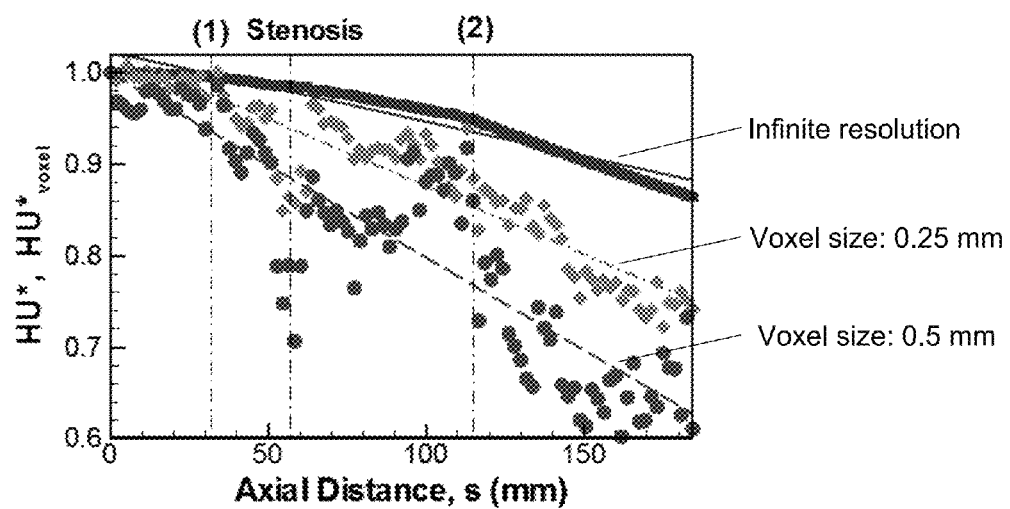
FIG. 8 illustrates a CFD simulated contrast concentration profile for a stenosis with 70% area constriction for different voxel resolutions, according to an embodiment of the present invention.

FIG. 8 illustrates CFD simulated normalized attenuation profiles for 70% area constriction for voxel resolutions of 0.5 mm³, 0.25 mm³, and the case for the theoretical profile with infinite spatial resolution. Decreasing spatial resolution (increased partial volume averaging) tends to cause overestimation of TAG. To account for the artificially higher TAG values that result due to partial volume effects as shown in FIG. 8, a correction factors, $\delta_1$, and $\delta_2$ can be implemented that accounts for the CTA voxel resolution. From computational simulations at multiple spatial resolutions and fixed taper, $\delta_1$ is approximately equal to 3.5 for the voxel resolution most typically used (approximately 0.4×0.4×0.4 mm).

$$\bar{Q} = \frac{\delta_1 \bar{A}}{-(TAG^* + \delta_2) \cdot T_d} \text{ (for linear AIF)}, \quad (25)$$

$$\bar{Q} = \frac{\pi}{T_d} \sqrt{\frac{\delta_1 \bar{A} V(\hat{s})}{-2(TAG^* + \delta_2)}} \text{ (for cosine AIF)}$$

Figure 9:
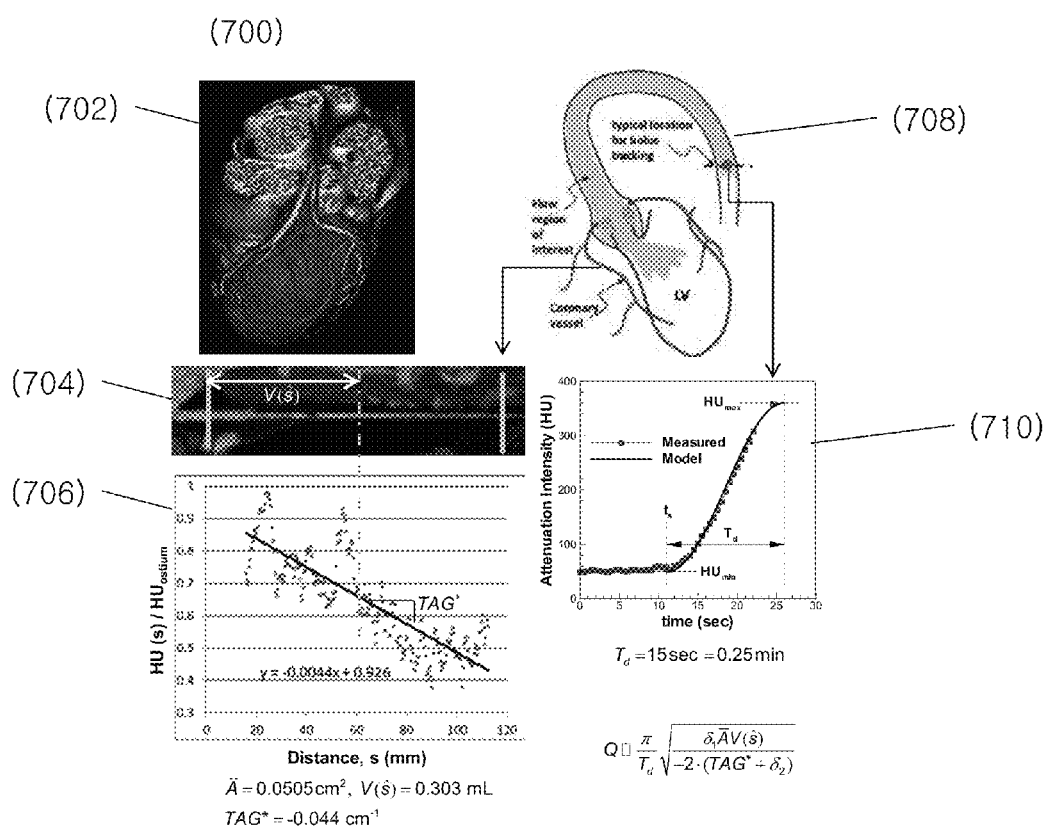
FIG. 9 illustrates a summary of the process for implementation of the current method according to an embodiment of the present invention.

By way of example, this section will outline the process of applying Eq. (25) to real-world CT angiography data for absolute flow measurement in a patient with LAD disease, as illustrated in FIG. 9. As indicated in Equation (25), after the 3D CT acquisition there are a total of 4 variables that need to be extracted from the CT data for flow calculation. Three of these variables ($\bar{A}$, V($\hat{s}$), TAG*) come directly from static CTCA images of the vessels, as illustrated in (704) and (706), and one variable ($T_d$) is derived from the AIF (temporal contrast concentration) following contrast injection shown in (708) and (710). To summarize the process in FIG. 9, following 3D isotemporal acquisition of the whole heart is illustrated in (702), multiplanar reformations of the three primary coronary vessels are generated that provide a straight vessel view as illustrated in (704). Software is then used to measure the luminal density as a function of vessel length between two user-defined proximal and distal boundary locations. The variable V(ŝ) is defined as the vessel volume from the ostium to the user-defined points and $\overline{A}$ is defined as the average cross-sectional area over the length of the vessel. TAG is defined as the slope of the normalized luminal density versus distance plot, as illustrated in (706). The temporal element of contrast dispersion needed for Equation (21) is taken from the time-density curve shown in (710) that is measured in the descending aorta, as illustrated in (708) prior to scanning to allow optimal timing or triggering of the CTA acquisition. While it is usually not used in standard CTCA, this temporal AIF data can be stored in the CT raw data and is easily reconstructed for the determination of $T_d$. The parameters for PVA correction, $\delta_1$ and $\delta_2$ which depend on the scanner and voxel resolution, may be determined by doing calibration test. Once all parameters have been isolated, Equation (25) can be used to calculate arterial flow.

In addition to CFD simulations to guide the formulation above, Equation (25) can also, for example, be used to calculate absolute blood flow in an ischemic canine model of LAD stenosis and in patients with obstructive and non-obstructive coronary artery disease. However, these applications are simply examples and are not to be considered limiting.

By way of example, the approach described in [0035] was applied to canine CT measurements. This data set consisted of 4 canine models of LAD stenosis that underwent CT imaging using a prototype 256-CT scanner with simultaneous microsphere injections. Despite the limited temporal resolution of this prototype scanner, image analysis and application of Equation (25) demonstrated resting coronary blood flow (LAD+LCx) of 29±10 ml/min. While coronary flow probes were not used in this study, this result is quite similar to direct probe-derived measurements in similar sized canines previously published, 31±8 ml/min.

Furthermore, there was a good correlation between flow derived from Eq. (25) and microsphere MBF (R=0.89, p<0.001). Thus, in the limited preclinical pilot data set, Equation (21) appears to provide the ability to accurately determine territorial flows supplied by the LAD and LCx and provides absolute total coronary flow values that are in agreement with those reported in the literature.

By way of example, the approach described in [0035] was applied to patient datasets. This clinical data set consisted of 9 patients enrolled in the CORE320 multicenter trial conducted at Johns Hopkins University. Patients in CORE320 underwent coronary CTA, stress CT and SPECT myocardial perfusion imaging. All AIF data was collected. FIG. 1 shows an AIF function for a patient included in this analysis demonstrating a perfect match of the linear or cosine AIF models, which gave further confidence to apply Equation (25) to the data set. Average total coronary flow (LAD+LCX+RCA) was 123.4±66 ml/min. When corrected for myocardial mass, total myocardial flow was 0.86±0.39 ml/g/min. These data are nearly identical with resting MBF seen in humans by O15-PET. When comparing patients with normal vs. abnormal perfusion by the reference standard (SPECT myocardial perfusion imaging), TAG alone showed no significant difference between ischemic and non-ischemic territories (p=0.93). However, when TAG was normalized by the density rise at the ostium and Equation (25) applied, there was a statistically significant difference in total coronary flow, 142 ml/min vs. 71 ml/min in normal and ischemic patients, respectively (p=0.04, See FIG. 9). Results from these preliminary data in human CT studies indicate Eq. (25) accurately measures coronary blood flow and can predict myocardial perfusion abnormalities determined by SPECT; while TAG, without accounting for the AIF, cannot.

Equation (25) has been derived for the specific types of AIF from simplified computational models and preliminary assessment of this expression against limited sets of canine and human data are highly promising and demonstrate feasibility. However, the expression can be further generalized to incorporate effects of arbitrary AIF and flow wave form function. In general the solution of the convection equation, Eq (1) can be given by $$\overline{C}(t,\eta) = C_{ostium}(t-\tau) \int_{t-\tau}^{t} Q(t) dt = \eta \quad (26)$$

where $\tau$ is a retarded time and Q(t) is arbitrary time varying flow rate. One can express the time varying flow rate and its time integral by the following forms;

$$Q(t) = \overline{Q} \cdot q(t), \int Q(t) dt = \overline{Q} \int q(t) dt = \overline{Q} \cdot g(t), \quad (27)$$

where $\overline{Q}$ is average flow rate. From Eqs. (3), (26) and (27) we can obtain the following expressions for the average flow rate;

$$\overline{Q} = \frac{\eta}{g(t) - g(\tau')}, \quad (28)$$

$$\overline{Q} = \frac{\overline{A}}{-TAG \cdot q(\tau')} \frac{\partial}{\partial t} C_{ostium}(\tau'),$$

where $\tau' = t - \tau$. Since the above system of equations has two unknowns; $\tau'$, $\overline{Q}$ if TAG is measured, it can be solved to find the average flow rate $\overline{Q}$ for any AIF and flow wave form. Thus the system of equations, Eq. (28) is the general TAFE formula for arbitrary AIF and flow wave form.

While FFR is considered the gold standard in assessment of stenosis, the methods described above could be applied to obtain other metrics of stenotic severity. In particular an estimate of the pressure gradient (PG) within the section of interest of the arterial network of the patient could be obtained using the arterial flow velocity, the arterial input function, information on the arterial luminal area, position and location within the artery; and once the pressure drop across the stenosis and the flow velocity are determined using the above method, the functional severity of the stenosis could also be determined in terms of a loss coefficient defined as $$K = \frac{\Delta P}{\frac{1}{2} \rho \left(\frac{Q}{A}\right)^2} \quad (29)$$

where Q is the flow rate upstream of the stenosis (obtained from TAFE) and A is the lumen area upstream of the stenosis. The advantage of the above measure is that it is virtually flow-rate independent and can be obtained with a single scan at rest condition (i.e. no need for a second scan at maximal hyperemia). The estimates of pressure drop across the stenosis may also be converted to FFR.

A method according to the present invention provides for obtaining a patient specific transluminal attenuation gradient (TAG) over a calcium-free section of the artery and determining a time variation of a contrast at a predetermined vascular or ventricular location (called the arterial input function or input bolus profile). The method also includes calculating an estimate of the fractional flow reserve (FFR) within the artery using the TAG and AIF and using the FFR to determine the functional significance of the arterial stenosis in vessels with severe calcification. The technique can include a method for correcting the TAG values for the effects of CT spatial resolution and partial volume averaging. The technique also includes a method for correcting the TAG values for the effects of vessel tortuosity, curvature and partial volume averaging. The method can also include protocol for determining a functional significance of arterial stenosis includes obtaining contrast concentration versus time data via a dynamic CT acquisition to calculate flow velocity.

The flow velocity may be obtained in the main artery as well as all of the sub branches for which contrast measurements are available. Thus, the method can provide the relative magnitude of the flow rate in the various branches and this information may be combined with other information or mathematical models to develop alternate measure of the functional significance of the coronary stenosis.

Figure 10:
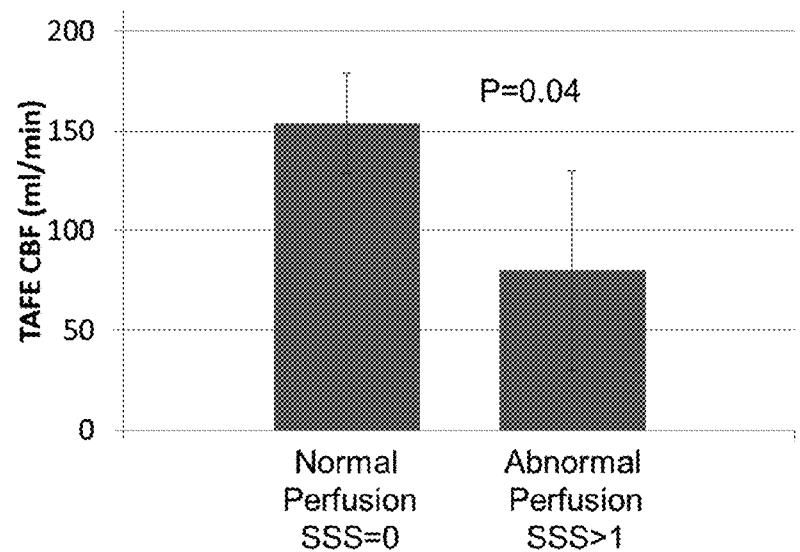
FIG. 10 illustrates graphs modeling results for specific patient data according to an embodiment of the present invention.
Figure 11:
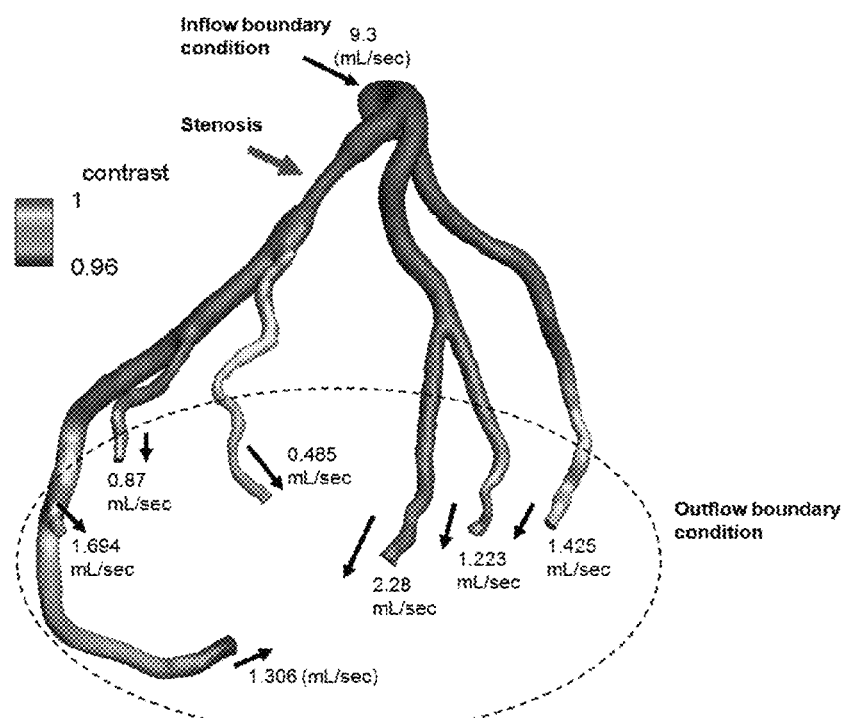
FIG. 11 illustrates a quantitative example of determining Q or TAFE, for the purposes of providing boundary conditions for CFD model according to an embodiment of the present invention

The flow velocity obtained from TAG (via TAFE) may be used to provide boundary or initial conditions for computational models (for example computational fluid dynamics (CFD) models) of the vasculature. The computational model could then be used to predict the pressure distribution and associated metrics such as FFR and PG. This eliminates the need for modeling of upstream (aorta, etc.) and downstream vasculature and reduces the computational expense and complexity of CFD based modeling. FIGS. 10 and 11 show an embodiment of this approach: TAFE takes contrast dispersion data from CTA and coverts it into flow-rate for all relevant vessels. These flow rates then generate inflow and outflow boundary conditions for a computational model.

The method described here could be used in normal vessels, in abnormal vessels as well as vessels subject to medical therapies such as medication, stents, grafts. The method can be applied in rest as well as other conditions such as stress (induced via exercise or medication).

The measurement of the contrast may be triggered by variety inputs including simultaneously measured ECG.

Figure 12:
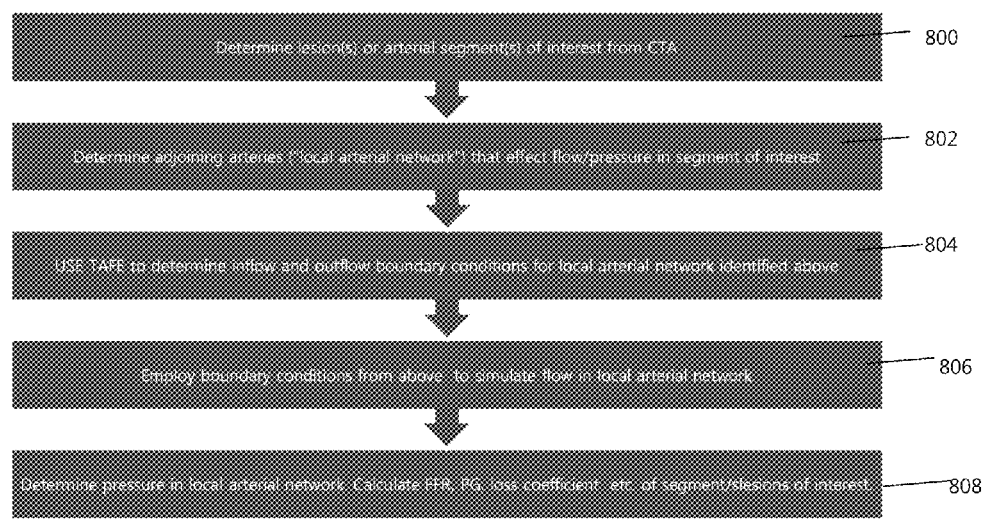
FIG. 12 illustrates a summary of the process for implementation of the current method for computational modeling (i.e. CFD calculation) according to an embodiment of the present invention.

FIG. 12 illustrates a summary of the process for implementation of the current method for computational modeling (i.e. CFD calculation) according to an embodiment of the present invention. Step 800 is determining a lesion or arterial segment of interest from CTA. In step 802 adjoining arteries in a local arterial network that effect flow or pressure in a segment of interest are determined. Step 804 includes using TAFE to determine inflow and outflow boundary conditions for the local arterial network identified above. In step 806 boundary conditions are used to simulate blood flow in the local arterial network, and in step 808 the pressure in the local arterial network is determined and FFR, PG, loss coefficient are determined for each segment or lesion of interest.

Figure 13:
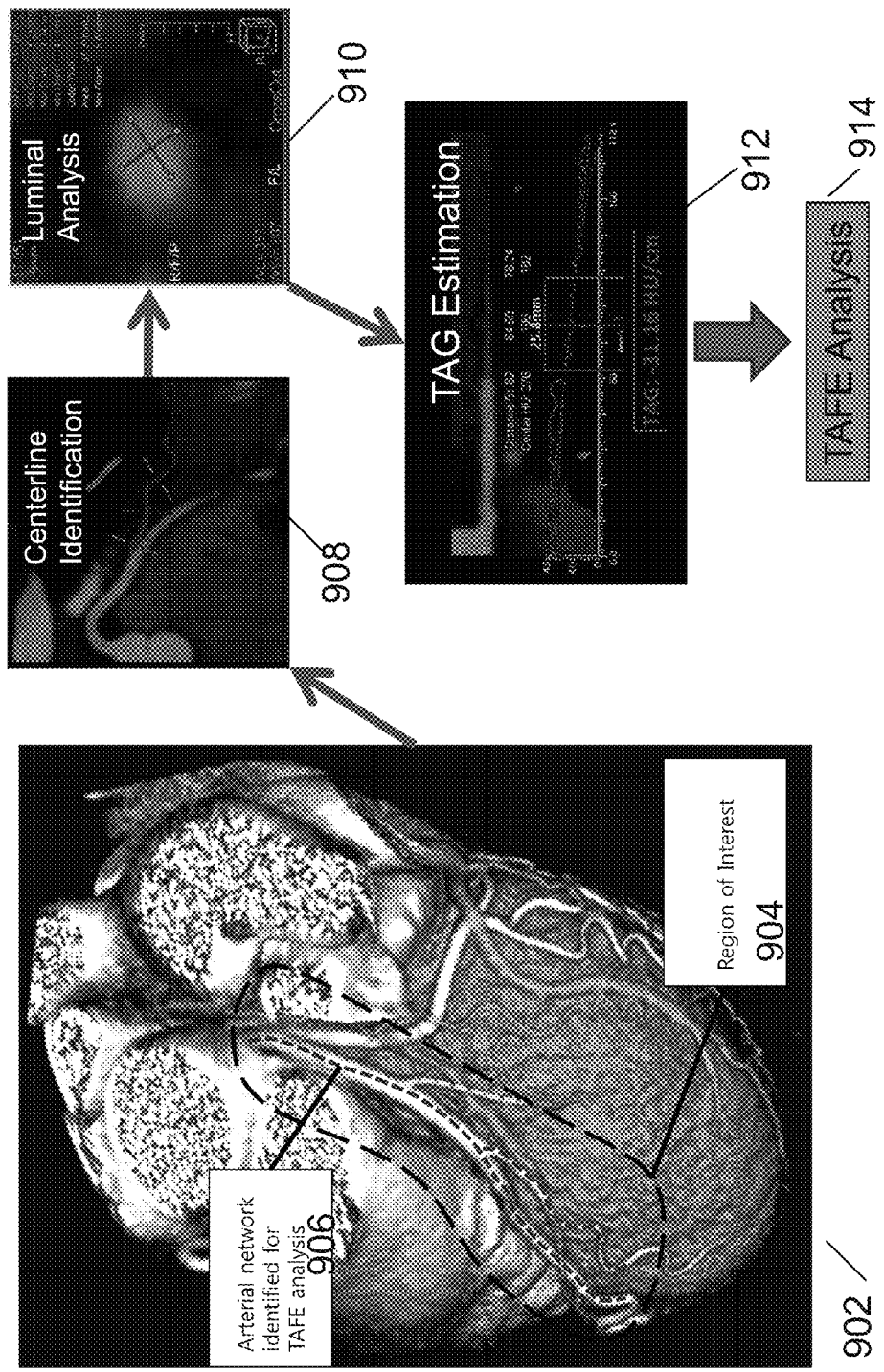
FIG. 13 illustrates a flow diagram of steps associated with converting contrast CT angiographic imaging data into TAFE-ready TAG information for a selected arterial network.

FIG. 13 illustrates a flow diagram of steps associated with converting contrast CT angiographic imaging data into TAFE-ready TAG information for a selected arterial network. Step 902 illustrates a region of interest 904 and an arterial network 906 disposed within the region of interest. The arterial network 906 is identified for TAFE analysis. In step 908 a centerline is identified for the arterial network identified for analysis. A luminal analysis is done in step 910. In step 912 this information is used to calculate a TAG estimation, and in step 914 a TAFE analysis is executed on the data.

Figure 14:
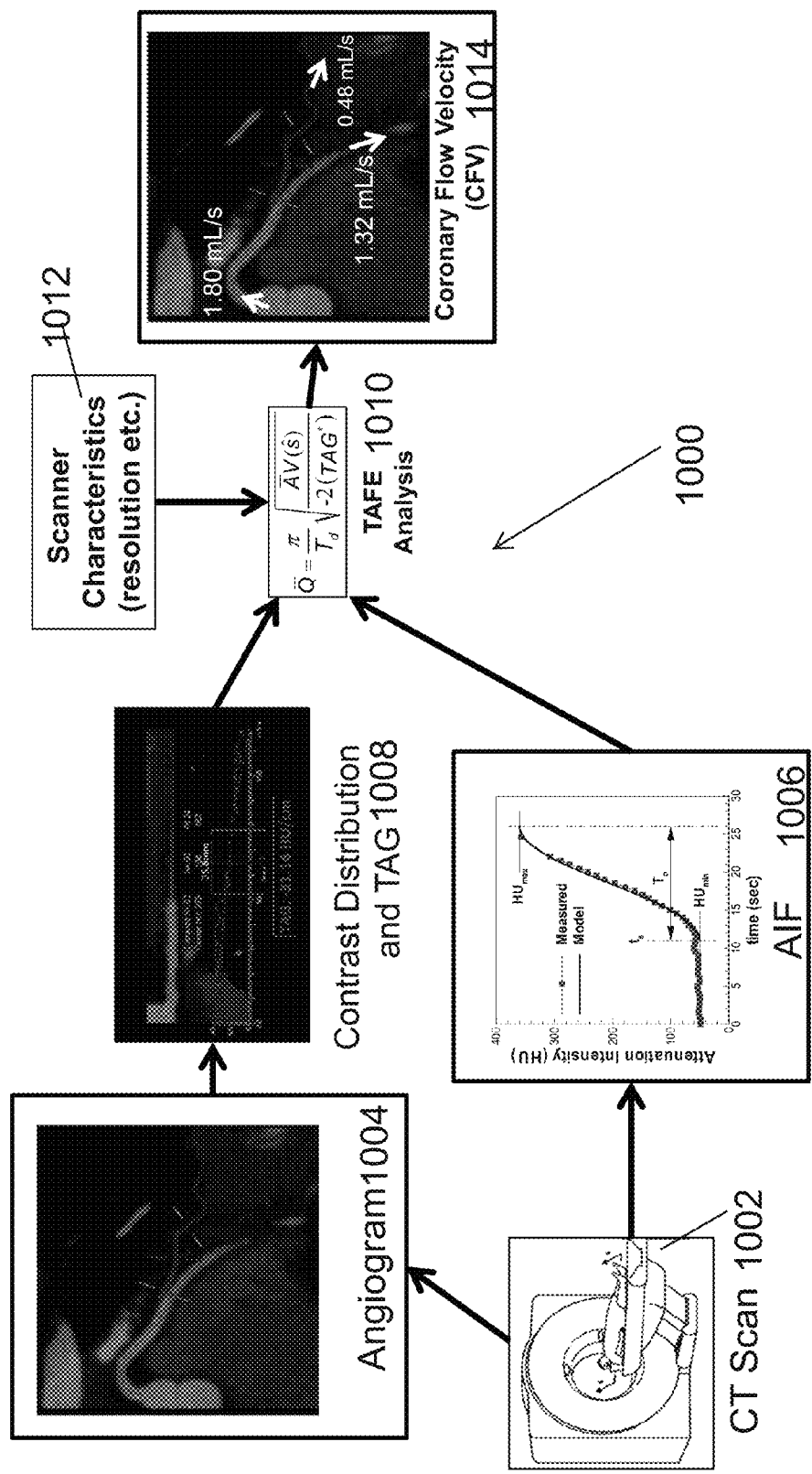
FIG. 14 illustrates a flow diagram of steps associated with obtaining CFV from TAFE for a selected area of interest of an arterial network.

FIG. 14 illustrates a flow diagram of steps associated with obtaining CFV from TAFE for a selected area of interest of an arterial network. In the flow diagram 1000, a CT scan is performed in step 1002 in order to gather data related to the patient. In step 1004 an angiogram is produced with the data related to the patient, and in step 1006 AIF is calculated and graphed using the data related to the patient. In step 1008, contrast distribution and TAG is calculated from the angiogram. TAG and AIF are used to calculate the TAFE analysis in step 1010. The TAFE analysis of step 1010 can also include input based on scanner characteristics, such as resolution, as noted in step 1012. The TAFE analysis is used to determine coronary flow velocity in step 1014.

Figure 15:
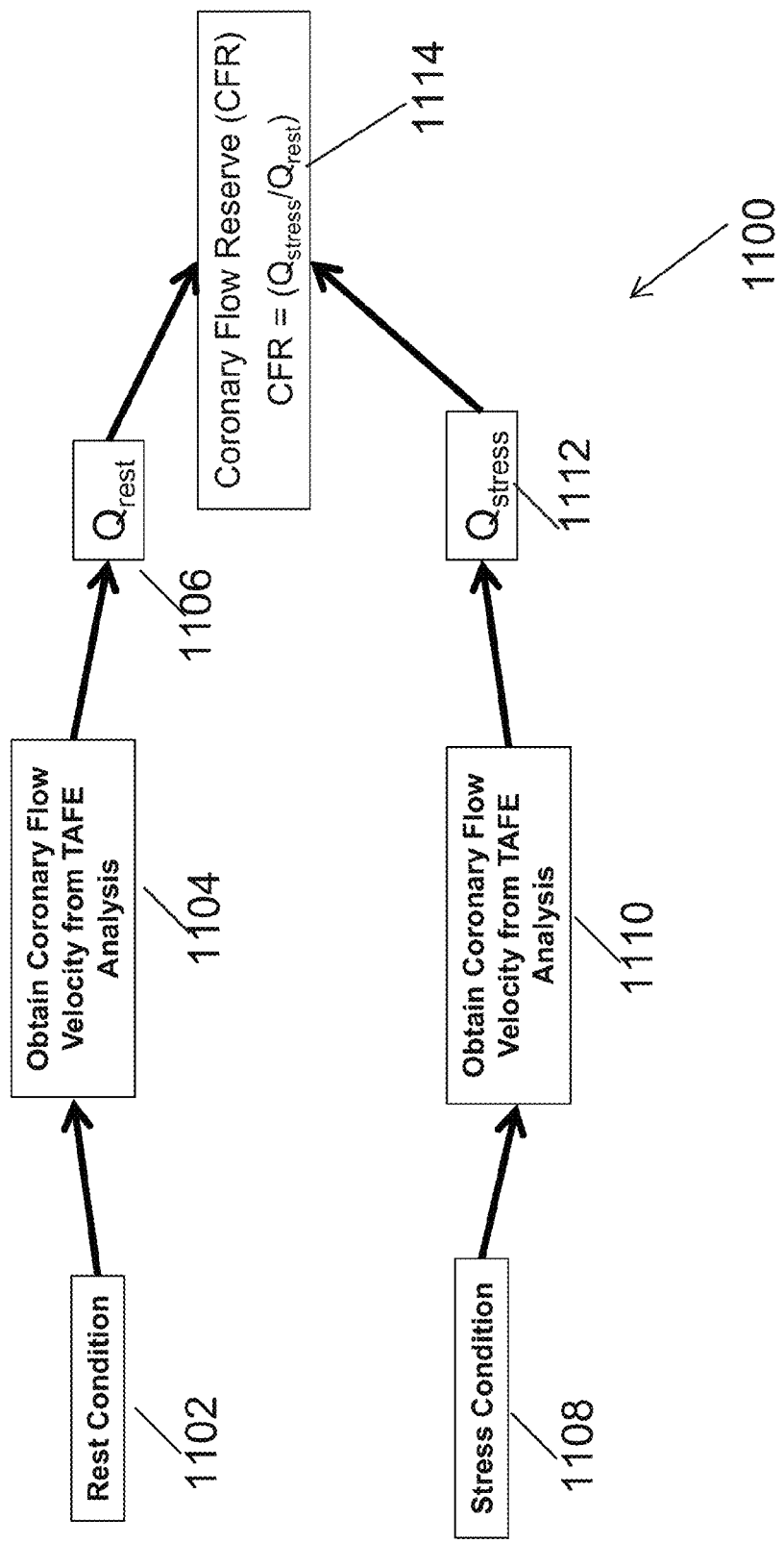
FIG. 15 illustrates a flow diagram of steps associated with determining coronary flow reserve from TAFE for arteries in the selected arterial network.

FIG. 15 illustrates a flow diagram of steps associated with determining coronary flow reserve from TAFE for arteries in the selected arterial network. In the flow diagram 1100, data must be obtained from the patient for the arterial network of interest, at both rest and stress. In step 1102, the patient is brought to a rest condition. In this state, coronary flow velocity is obtained from a TAFE analysis, as described above, in step 1104. In step 1106, $Q_{rest}$ is determined, also as described above. In step 1108, the patient is brought into a stress condition. In the stress state, coronary flow velocity is obtained from a TAFE analysis, as described above, in step 1110. In step 1112, $Q_{stress}$ is determined, also as described above. Coronary flow reserve (CFR) is determined in step 1114, as the ratio between $Q_{stress}$ and $Q_{rest}$.

Figure 16:
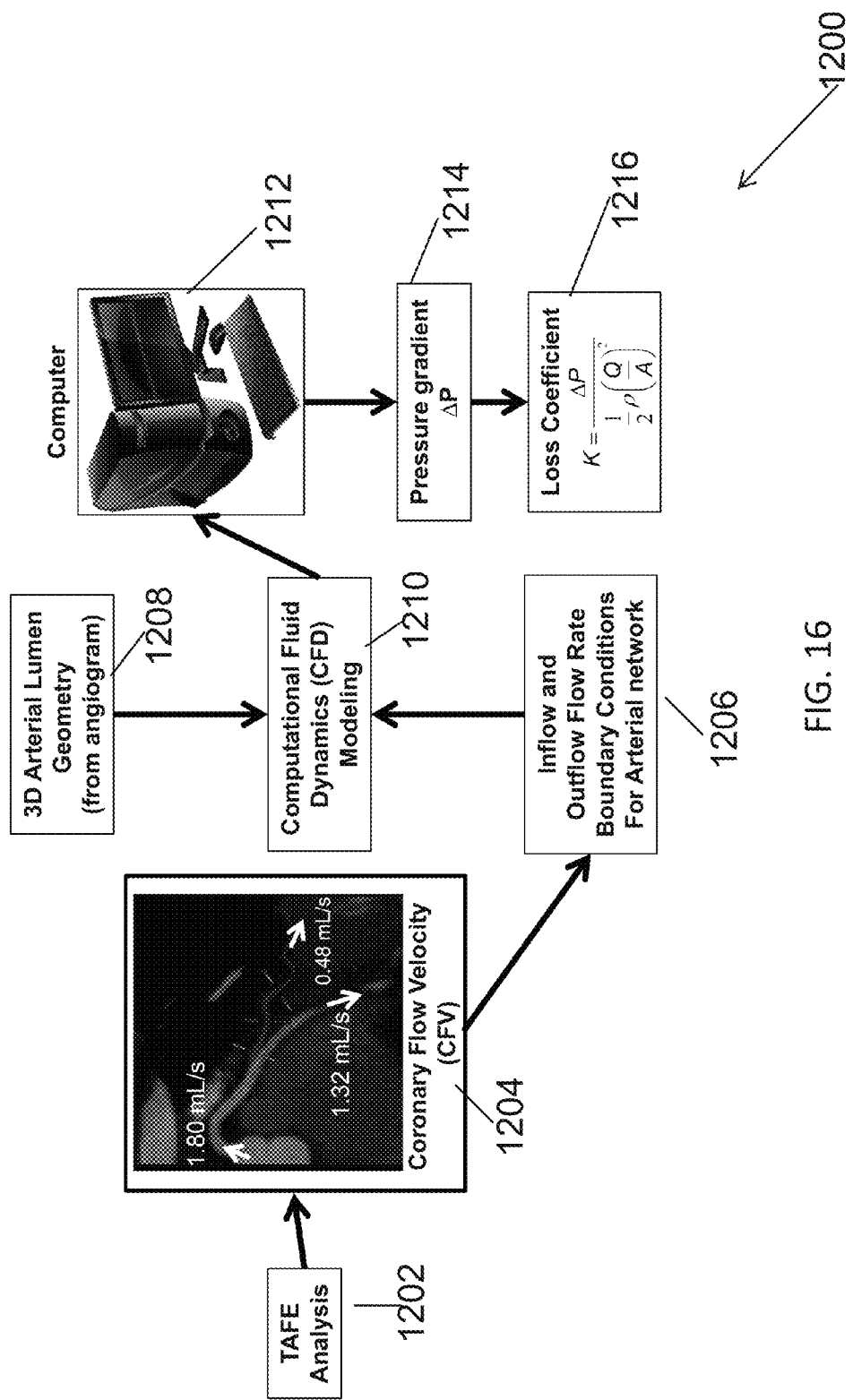
FIG. 16 illustrates a flow diagram of steps associated with obtaining pressure gradient (PG) and loss coefficient (K) from TAFE for arteries in the area of interest in the selected arterial network.

FIG. 16 illustrates a flow diagram of steps associated with obtaining pressure gradient (PG) and loss coefficient (K) from TAFE for arteries in the area of interest in the selected arterial network. In the flow diagram 1200, the TAFE analysis process described above, is executed in step 1202. In step 1204, the TAFE analysis is used to determine coronary flow velocity, also as described above. In step 1206, inflow and outflow rate boundary conditions are determined for the area of interest in the selected arterial network. 3D arterial lumen geometry is calculated from the angiogram and in step 1208, the 3D arterial lumen geometry and the information about CFV and inflow and outflow rate boundary conditions are used to execute computational fluid dynamics (CFD) modeling of the arterial network of interest, in step 1210. A computing device, server, tablet, smartphone, or other computer can be used to execute these steps, as illustrated in step 1212. Pressure gradient ($\Delta P$) is calculated in step 1214 and loss coefficient is calculated in step 1216, using EQ. 29.

Figure 17:
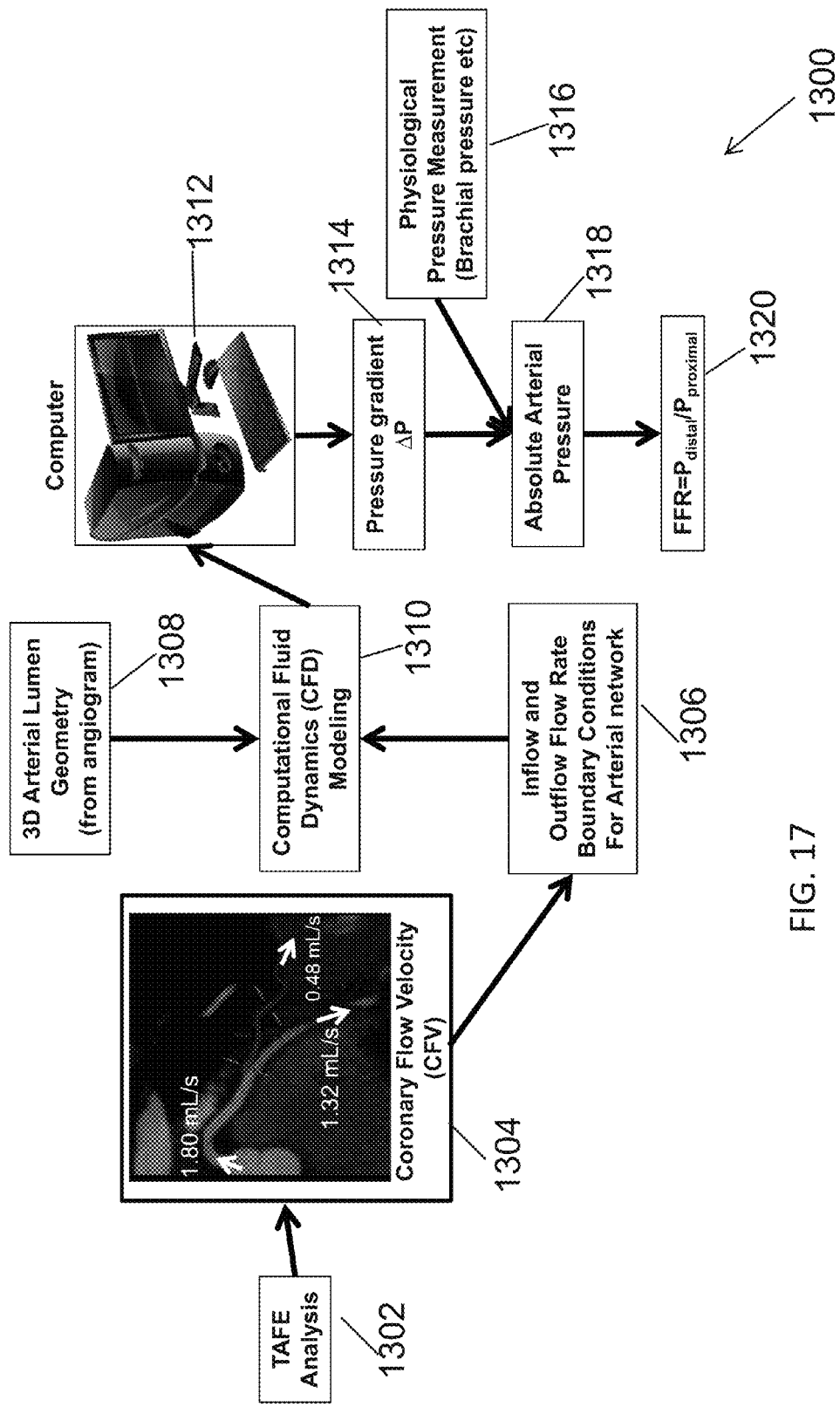
FIG. 17 illustrates a process of obtaining FFR from TAFE for arteries in the area of interest of the selected arterial network.

FIG. 17 illustrates a process of obtaining FFR from TAFE for arteries in the area of interest of the selected arterial network. In the flow diagram 1300, the TAFE analysis process described above, is executed in step 1302. In step 1304, the TAFE analysis is used to determine coronary flow velocity, also as described above. In step 1306, inflow and outflow rate boundary conditions are determined for the area of interest in the selected arterial network. 3D arterial lumen geometry is calculated from the angiogram and, in step 1308, the 3D arterial lumen geometry and the information about CFV and inflow and outflow rate boundary conditions are used to execute computational fluid dynamics (CFD) modeling, in step 1310. A computing device, server, tablet, smartphone, or other computer can be used to execute these steps, as illustrated in step 1312. Pressure gradient ($\Delta P$) is calculated in step 1314. In step 1316, physiological pressure measurements, such as brachial pressure are obtained. The pressure gradient ($\Delta P$) and the physiological pressure measurements are used to estimate absolute pressure at the coronary ostium and combined with the CFD modeling to calculate absolute arterial pressure in the artery of interest in step 1318. In step 1320, FFR is calculated as the ratio between $P_{distal}$ and $P_{proximal}$.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method for determining functional significance of an arterial stenosis or lesion in a patient comprising:
    determining an area of interest of an arterial network of the patient;
    obtaining a computed tomography (CT) scan of the patient during an angiogram procedure, resulting in data on the area of interest;
    performing correction of the data obtained from the CT scan for partial volume-averaging resulting in corrected image data;
    generating and displaying a corrected image using the corrected image data;
    using the corrected image data to calculate an arterial input function (AIF) for the area of interest;
    using the corrected image data to determine contrast distribution and transluminal attenuation gradient (TAG) for the area of interest;
    calculating transluminal attenuation flow encoding (TAFE) using contrast distribution, TAG, and AIF;
    modeling coronary flow velocity through the area of interest of the arterial network using TAFE; and,
    generating and displaying a coronary flow velocity image of the area of interest to allow for identification of the arterial stenosis or lesion within the area of interest.

2. The method of claim 1 further comprising augmenting the calculation of TAFE with data related to characteristics of a scanner used to obtain the CT scan.

3. The method of claim 1 further comprising programming a non-transitory computer readable medium to execute the method.

4. The method of claim 1 further comprising bringing the patient to a cardiac rest condition before obtaining the CT scan of the patient during the angiogram.

5. The method of claim 4 further comprising calculating the coronary flow velocity for the area of interest for the patient at the cardiac rest condition.

6. The method of claim 1 further comprising bringing the patient to a cardiac stressed condition before obtaining the CT scan of the patient during the angiogram.

7. The method of claim 6 further comprising calculating the coronary flow velocity for the area of interest for the patient at the cardiac stress condition.

8. The method of claim 1 further comprising obtaining a CT scan of the patient during an angiogram with the patient at cardiac rest and obtaining a CT scan of the patient during an angiogram with the patient under cardiac stress.

9. The method of claim 6 further comprising calculating coronary flow rate through the area of interest of the arterial network for the patient at cardiac rest and under cardiac stress.

10. The method of claim 7 further comprising calculating coronary flow reserve for the area of interest as a ratio of flow rate under cardiac stress to flow rate under cardiac rest ($Q_{stress}$ to $Q_{rest}$).

11. A method for determining functional significance of an arterial stenosis or lesion in a patient comprising:
    determining an area of interest of an arterial network of the patient;
    obtaining a computed tomography (CT) scan of the patient during an angiogram procedure, resulting in data on the area of interest;
    performing correction of the data obtained from the CT scan for partial volume-averaging resulting in corrected image data;
    generating and displaying a corrected image using the corrected image data;
    using the corrected data to calculate an arterial input function (AIF) for the area of interest;
    using the corrected data to determine contrast distribution and transluminal attenuation gradient (TAG) for the area of interest;
    calculating transluminal attenuation flow encoding (TAFE) using contrast distribution, TAG, and AIF;
    modeling coronary flow velocity using TAFE;
    using the coronary flow velocity to determine inflow and outflow rate and boundary conditions for the area of interest;
    determining a 3D arterial lumen geometry;
    generating and displaying a 3D arterial lumen image of the area of interest to allow for identification of the arterial stenosis or lesion within the area of interest;
    performing computational fluid dynamics (CFD) modeling for the area of interest using the boundary conditions, inflow and outflow rates, and the 3D arterial lumen geometry;
    calculating a pressure gradient for the area of interest using the CFD model; and,
    using the pressure gradient to determine a loss coefficient for the area of interest.

12. The method of claim 11 further comprising augmenting the calculation of TAFE with data related to characteristics of a CT scanner used to obtain the CT scan.

13. The method of claim 11 further comprising programming a non-transitory computer readable medium to execute the method.

14. A method for determining functional significance of an arterial stenosis or lesion in a patient comprising:
    determining an area of interest an arterial network of the patient;
    obtaining a computed tomography (CT) scan of the patient during an angiogram procedure, resulting in data on the area of interest;
    performing correction of the data obtained from the CT scan for partial volume-averaging resulting in corrected image data;
    generating and displaying a corrected image using the corrected image data;
    using the corrected data to calculate an arterial input function (AIF) for the area of interest;
    using the corrected data to determine contrast distribution and transluminal attenuation gradient (TAG) for the area of interest;
    calculating transluminal attenuation flow encoding (TAFE) using contrast distribution, TAG, and AIF;
    modeling coronary flow velocity through the area of interest of the arterial network using TAFE;
    generating and displaying a coronary flow velocity image of the area of interest to allow for identification of the arterial stenosis or lesion within the area of interest;
    using the coronary flow velocity to determine inflow and outflow rate and boundary conditions for the area of interest;
    determining a 3D arterial lumen geometry;
    generating and displaying a map of the 3D arterial lumen geometry;

performing computational fluid dynamics (CFD) modeling for the area of interest using the boundary conditions, inflow and outflow rates, and the 3D arterial lumen geometry;

calculating a pressure gradient for the area of interest using the CFD model;

using the pressure gradient to determine a loss coefficient for the area of interest;

measuring brachial pressure;

calculating an absolute arterial pressure; and, calculating fractional flow reserve at cardiac rest for the patient.

15. The method of claim 14 further comprising augmenting the calculation of TAFE with data related to characteristics of a CT scanner used to obtain the CT scan.

16. The method of claim 14 further comprising programming a non-transitory computer readable medium to execute the method.

17. A system for determining functional significance of an arterial stenosis or lesion in a patient comprising:

a computed tomography (CT) scanner configurable to obtain patient specific data related to an area of interest of an arterial network of the patient;

a non-transitory computer readable medium programmed for:

determining an area of interest of an arterial network of the patient;

obtaining the patient specific data on the area of interest;

performing correction of the patient specific data obtained from the CT scan for partial volume-averaging resulting in corrected image data;

generating and displaying a corrected image using the corrected image data;

using the corrected data to calculate an arterial input function (AIF) for the area of interest;

using the corrected data to determine contrast distribution and transluminal attenuation gradient (TAG) for the area of interest;

calculating transluminal attenuation flow encoding (TAFE) using contrast distribution, TAG, and AIF;

modeling coronary flow velocity using TAFE; and, generating and displaying a coronary flow velocity image of the area of interest to allow for identification of the arterial stenosis or lesion within the area of interest.

18. The system of claim 17 further comprising obtaining patient specific data during an angiogram with the patient at cardiac rest and obtaining patient specific data during an angiogram with the patient under cardiac stress.

19. The system of claim 18 further comprising calculating flow rate for the patient at cardiac rest and under cardiac stress.

20. The system of claim 17 further comprising calculating coronary flow reserve for the area of interest as a ratio of flow rate under cardiac stress to flow rate under cardiac rest ($Q_{stress}$ to $Q_{rest}$).

21. The system of claim 17 further comprising:

using the coronary flow velocity to determine inflow and outflow rate and boundary conditions for the area of interest;

determining a 3D arterial lumen geometry;

performing computational fluid dynamics (CFD) modeling for the area of interest using the boundary conditions, inflow and outflow rates, and the 3D arterial lumen geometry;

calculating a pressure gradient for the area of interest using the CFD model; and, using the pressure gradient to determine a loss coefficient for the area of interest.

22. The system of claim 21 further comprising:

measuring brachial pressure;

calculating an absolute arterial pressure; and, calculating fractional flow reserve at cardiac rest for the patient.

* * * * *